US012076157B2

(12) United States Patent
Knuebel et al.

(10) Patent No.: US 12,076,157 B2
(45) Date of Patent: Sep. 3, 2024

(54) METHOD AND DEVICE FOR DETERMINING A DEGREE OF DAMAGE OF HAIR, AND METHOD FOR DETERMINING A USER-SPECIFIC HAIR TREATMENT AGENT

(71) Applicant: Henkel AG & Co. KGaA, Duesseldorf (DE)

(72) Inventors: Georg Knuebel, Duesseldorf (DE); Meike Voss-Klimke, Langenfeld (DE); Oliver Seiler, Duesseldorf (DE); Ludger Buetfering, Nideggen-Rath (DE); Asrtid Kroos, Monheim (DE); Annika Koenen, Grevenbroich (DE)

(73) Assignee: HENKEL AG & CO. KGAA, Duesseldorf (DE)

(*) Notice: Subject to any disclaimer, the term of this patent is extended or adjusted under 35 U.S.C. 154(b) by 1624 days.

(21) Appl. No.: 16/311,873

(22) PCT Filed: Jul. 4, 2017

(86) PCT No.: PCT/EP2017/066572
§ 371 (c)(1),
(2) Date: Dec. 20, 2018

(87) PCT Pub. No.: WO2018/007353
PCT Pub. Date: Jan. 11, 2018

(65) Prior Publication Data
US 2019/0192067 A1 Jun. 27, 2019

(30) Foreign Application Priority Data
Jul. 5, 2016 (DE) .................... 10 2016 212 202.9

(51) Int. Cl.
*A61B 5/00* (2006.01)
*A45D 44/00* (2006.01)
(Continued)

(52) U.S. Cl.
CPC .............. *A61B 5/448* (2013.01); *A45D 44/00* (2013.01); *A61B 5/0075* (2013.01);
(Continued)

(58) Field of Classification Search
CPC ..... A61B 5/448; A61B 5/0075; A61B 5/1032; A61B 5/7246; A61B 2560/0223; A45D 2044/007
See application file for complete search history.

(56) References Cited

U.S. PATENT DOCUMENTS 5,100,436 A * 3/1992 Wenke ..................... A61K 8/19
8/408
5,753,214 A * 5/1998 Yoshioka ................. A61K 8/64
424/70.2

(Continued)

FOREIGN PATENT DOCUMENTS

CN 101686819 A 3/2010
CN 103608666 A 2/2014

(Continued)

OTHER PUBLICATIONS

EPO, International Search Report issued in International Application No. PCT/EP2017/066572, dated Oct. 5, 2017.

(Continued)

*Primary Examiner* — Baisakhi Roy
(74) *Attorney, Agent, or Firm* — Lorenz & Kopf, LLP

(57) ABSTRACT

Disclosed is a method with different exemplary embodiments for determining a degree of damage to hair. Said method can comprise the following steps: during the exposure of a hair sample to near-infrared and/or infrared light, recording a spectrum of at least part of the near-infrared and/or infrared light that has interacted with the hair sample, comparing at least part of the spectrum with a spectroscopic calibration model obtained by near-infrared and/or infrared (Continued)

spectra and degrees of damage of a plurality of calibration hair samples, and determining the degree of damage to the hair using said comparison.

13 Claims, 5 Drawing Sheets

(51) Int. Cl.
*A61B 5/103* (2006.01)
*A61B 5/145* (2006.01)
*A61B 5/1455* (2006.01)
*G01J 3/02* (2006.01)
*G01N 21/359* (2014.01)
*G16H 20/00* (2018.01)
*G01J 3/28* (2006.01)

(52) U.S. Cl.
CPC .......... *A61B 5/1032* (2013.01); *A61B 5/7246* (2013.01); *G01J 3/0272* (2013.01); *G16H 20/00* (2018.01); *A45D 2044/007* (2013.01); *A61B 2503/12* (2013.01); *A61B 2560/0223* (2013.01); *G01J 3/28* (2013.01)

(56) References Cited

U.S. PATENT DOCUMENTS

| | | | | |
|---|---|---|---|---|
| 8,986,939 B1* | 3/2015 | Hill | ................ | G01N 33/946 |
| | | | | 435/7.9 |
| 11,035,801 B2* | 6/2021 | Knuebel | ................ | G01N 21/25 |
| 11,457,859 B2* | 10/2022 | Knuebel | ................ | G01N 21/359 |
| 11,534,106 B2* | 12/2022 | Knuebel | ................ | A61B 5/1032 |
| 2002/0010556 A1 | 1/2002 | Marapane | | |
| 2003/0025360 A1 | 2/2003 | Liu | | |
| 2006/0281994 A1* | 12/2006 | Miyamae | ........... | G01N 21/3563 |
| | | | | 600/473 |
| 2008/0279804 A1* | 11/2008 | Parker | ................ | A61K 8/25 |
| | | | | 424/70.11 |
| 2015/0265525 A1* | 9/2015 | Benn | ................ | A61Q 5/10 |
| | | | | 206/568 |
| 2016/0287502 A1* | 10/2016 | Goutsis | ................ | A45D 7/04 |
| 2017/0292908 A1* | 10/2017 | Wilk | ................ | G01N 21/359 |

FOREIGN PATENT DOCUMENTS

| | | | | |
|---|---|---|---|---|
| CN | 104203207 A | | 12/2014 | |
| JP | 2003270138 A | * | 9/2003 | ............ G01N 21/35 |
| JP | 2003344279 A | * | 12/2003 | ............ G01N 33/50 |
| JP | WO2005096938 A1 | * | 10/2005 | ............ A61B 5/107 |
| WO | 2015166403 A1 | | 11/2015 | |

OTHER PUBLICATIONS

Koji Takada et al: "Influence of Oxidative and/or Reductive Treatment on Human Hair (I): Analysis of Hair-Damage after Oxidative and/or Reductive Treatment", Journal of Oleo Science, vol. 52, No. 10, Jan. 1, 2003 (Jan. 1, 2003), pp. 541-548, XP055002836, ISSN: 1345-8957.

* cited by examiner

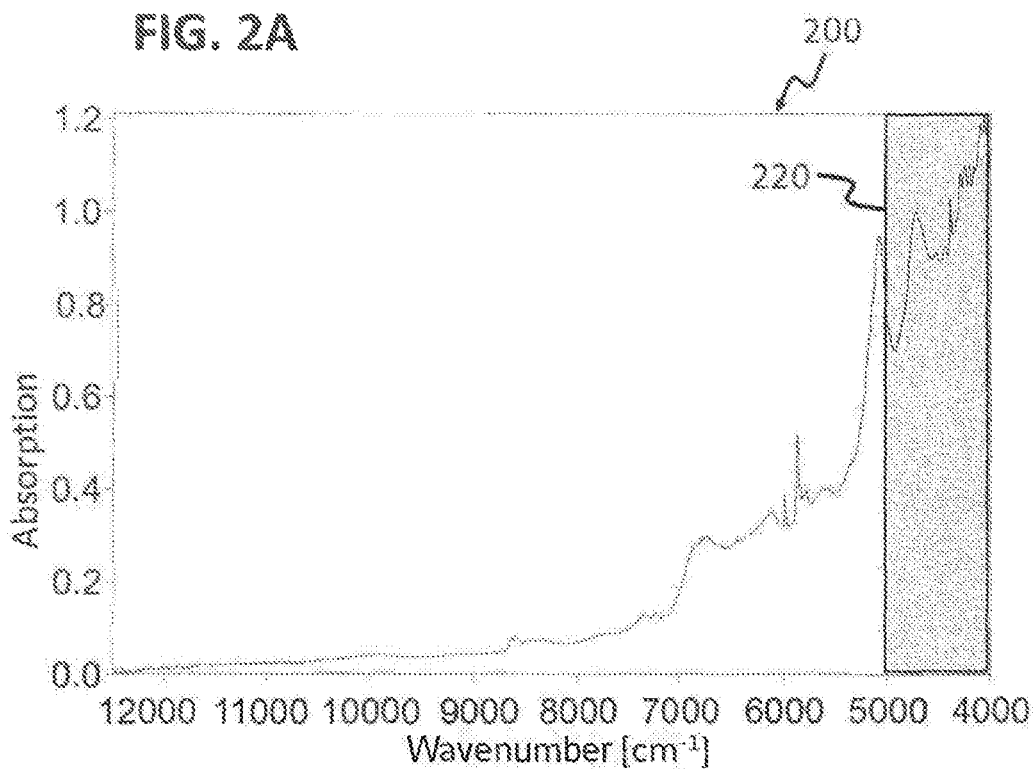
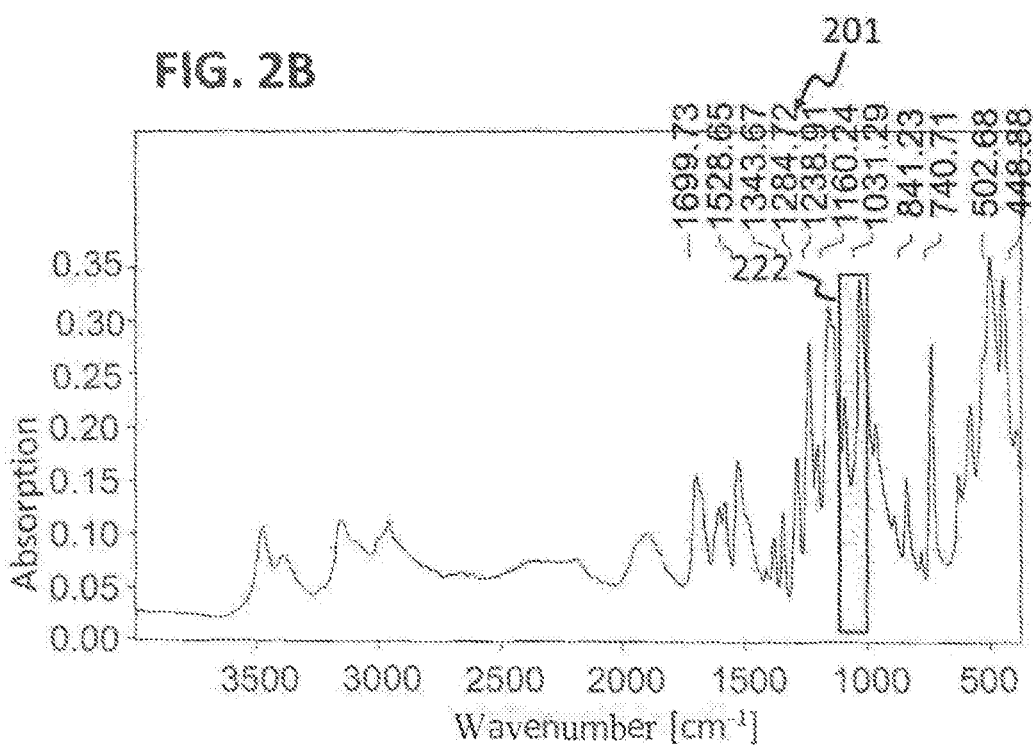

| Probe | Reference Gew.% Cysteic | NIR Value Gew.% Cysteic |
|---|---|---|
| A0 | 0.60 | 0.62 |
| A1 | 1.70 | 1.33 |
| A2 | 2.50 | 2.38 |
| A4 | 4.40 | 3.88 |
| A5 | 5.10 | 4.81 |
| A6 | 5.60 | 5.24 |
| A7 | 6.30 | 6.11 |
| A8 | 7.50 | 7.00 |
| A9 | 7.60 | 7.38 |
| A10 | 8.30 | 8.28 |
| A11 | 8.90 | 9.31 |
| A12 | 9.80 | 9.43 |
| A 9-2 | 7.60 | 7.14 |
| A10-2 | 8.30 | 8.00 |
| A11-2 | 8.90 | 9.00 |
| A12-2 | 9.80 | 9.30 |

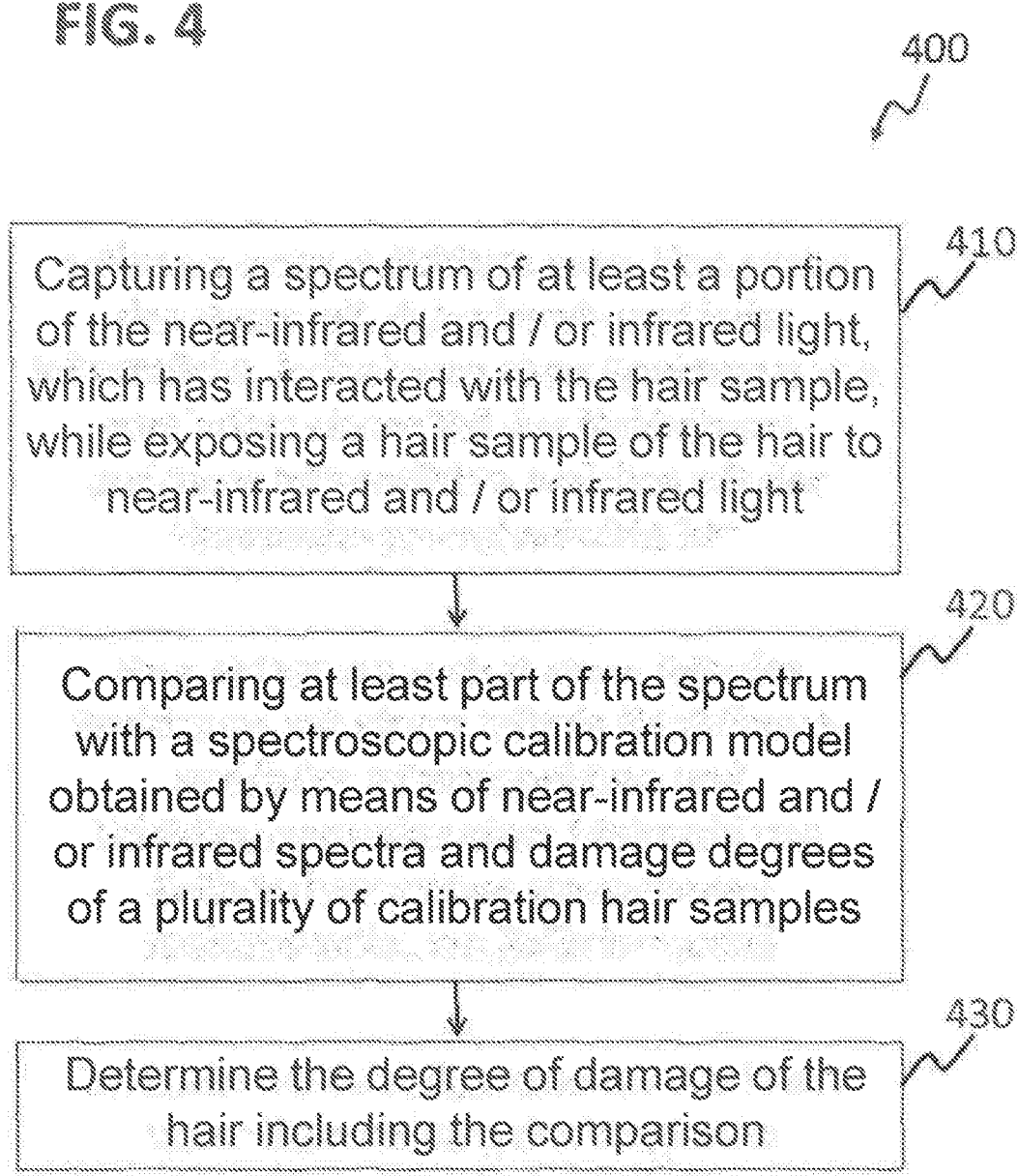

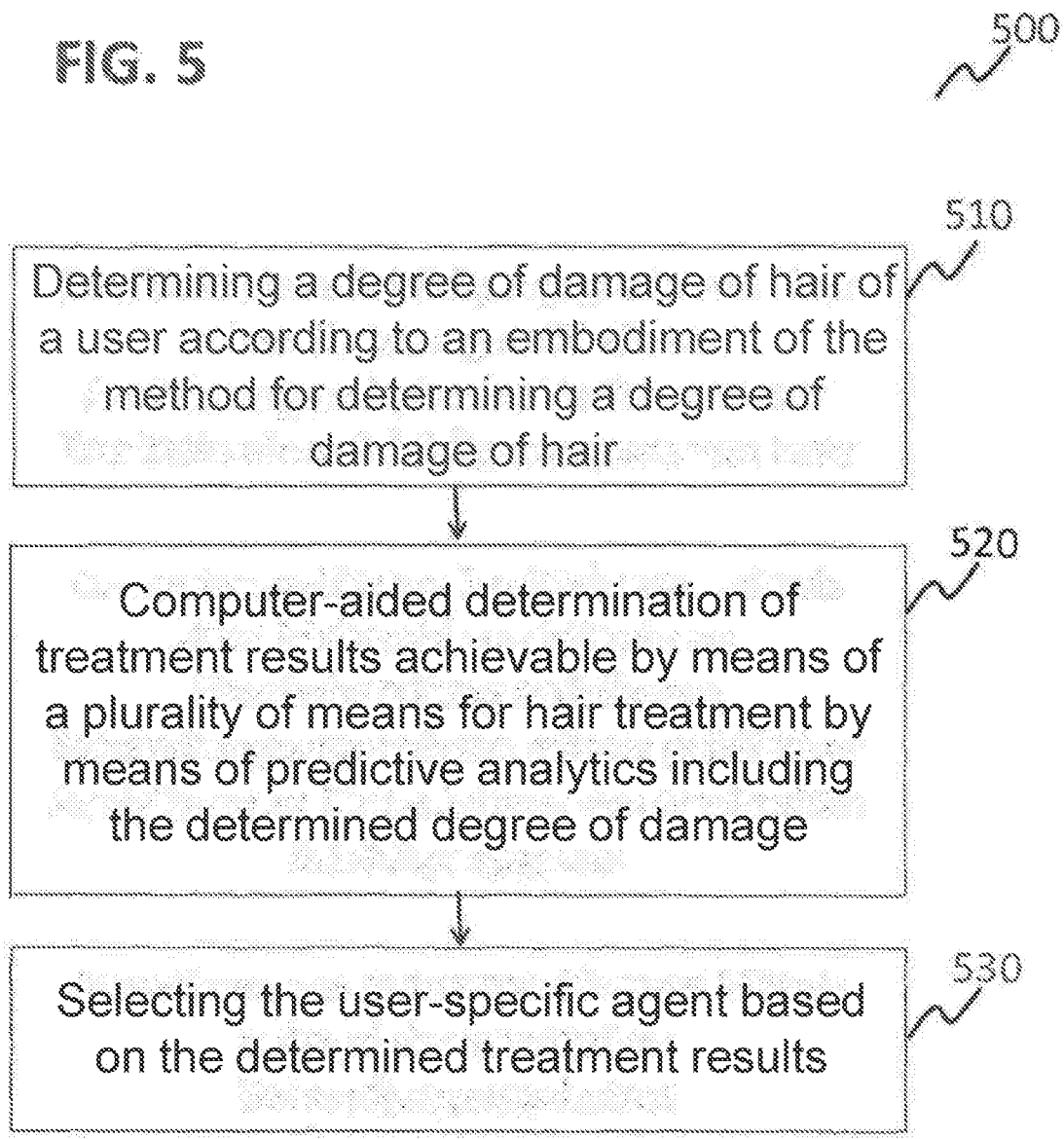

METHOD AND DEVICE FOR DETERMINING A DEGREE OF DAMAGE OF HAIR, AND METHOD FOR DETERMINING A USER-SPECIFIC HAIR TREATMENT AGENT

CROSS-REFERENCE TO RELATED APPLICATION

This application is a U.S. National-Stage entry under 35 U.S.C. § 371 based on International Application No. PCT/EP2017/066572, filed Jul. 4, 2017 which was published under PCT Article 21(2) and which claims priority to German Application No. 10 2016 212 202.9, filed Jul. 5, 2016, which are all hereby incorporated in their entirety by reference.

TECHNICAL FIELD

The present disclosure relates to a method and a device for determining a degree of damage of hair, and a method for determining a user-specific hair treatment agent.

BACKGROUND

In a treatment of hair with cosmetic products, an effect of the product, for example an intensity of a coloration, may be heavily dependent on the degree of damage of the hair.

It may therefore be of great importance to determine any damage of the hair.

Hair can be damaged by natural or artificially induced processes. The most important type of damage here may be oxidative damage.

The natural processes for example may include a combined (for example simultaneous) effect of UV light and oxygen ($O_2$) on the hair.

The artificially induced processes for example may include the application of hair dyes (also referred to as colorants), bleaching and/or production of a permanent wave.

Here, besides desired cosmetic effects, such as a lightening of the hair, significant damage of the hair may also occur, for example when oxidants are used.

The damage process may occur here as a result of the oxidation of amino acids, for example oxidation of the amino acids cystine and cysteine, which occur frequently in the hair, to form cysteic acid. Cystine can form intermolecular disulfide bridges (also referred to as S-S bridges) in the hair, and therefore cystine is extremely important for the mechanical stability of the hair, The oxidation of these bridges to form cysteic acid can destroy the mechanical stability of hair and, in the event of multiple applications, can even lead to complete hair breakage. However, before macroscopically observable, tactile properties of the hair may be negatively influenced, for example a surface roughness may be present. Furthermore, hair damage can be dramatic at even an early stage of injury as compared to undamaged hair as a results of cosmetic treatments.

The described mechanism of damage makes it possible to exactly determine the degree of the most important damage, specifically the oxidative damage, by determining the content of cysteic acid.

In an academic and industrial field, there are a large number of physical and chemical-analytic methods available to a researcher or developer for performing a determination of the degree of damage, for example a quantitative determination of the degree of oxidative damage.

Usually, chromatographic methods are used here, such as high-performance liquid chromatography (HPLC) after a complex acidic hydrolytic decomposition of the hair sample.

Undamaged hair can typically have a cysteic acid content in a range of from approximately 0.5% to approximately 1% (based on weight). If there is damage, for example as a result of repeated ultra-bleaching and/or other mechanisms of damage, the cysteic acid content may be increased to more than 15% (by weight).

However, all of these chromatography methods are complicated and require a costly equipment set-up, such that they are not available to an end consumer.

Damaging cosmetic treatments, for example hair colorations, applications of heat, permanent waving or oxidative procedures, such as bleaching, and many others, are typically performed on the end consumer in the private field or in the field of commercial services. Although the performance of a further damaging procedure on hair that is already damaged may lead to catastrophic results, going as far as complete hair breakage, there was not previously any possibility within this scope to determine the degree of prior damage of the hair, for example quantitatively.

BRIEF SUMMARY

A method for determining a degree of damage of hair is provided herein. The method includes the step of, during the exposure of a hair sample to near-infrared and/or infrared light, recording a spectrum of at least part of the near-infrared and/or infrared light that has interacted with the hair sample. The method further includes the step of comparing at least part of the spectrum with a spectroscopic calibration model obtained by near-infrared and/or infrared spectra and degrees of damage of a plurality of calibration hair samples. The method further includes the step of determining the degree of damage of the hair on consideration of the comparison.

BRIEF DESCRIPTION OF DRAWINGS

The present disclosure will hereinafter be described in conjunction with the following drawing figures, wherein like numerals denote like elements, and:

FIGS. 2A and 2B show near-infrared (FIG. 2A) and infrared (FIG. 2B) spectra of cysteic acid;

FIG. 4 shows a flow diagram illustrating a method for determining a degree of damage of hair in accordance with various exemplary embodiments; and FIG. 5 shows a flow diagram illustrating a method for determining a user-specific hair treatment agent in accordance with various exemplary embodiments.

DETAILED DESCRIPTION

Figure 1:
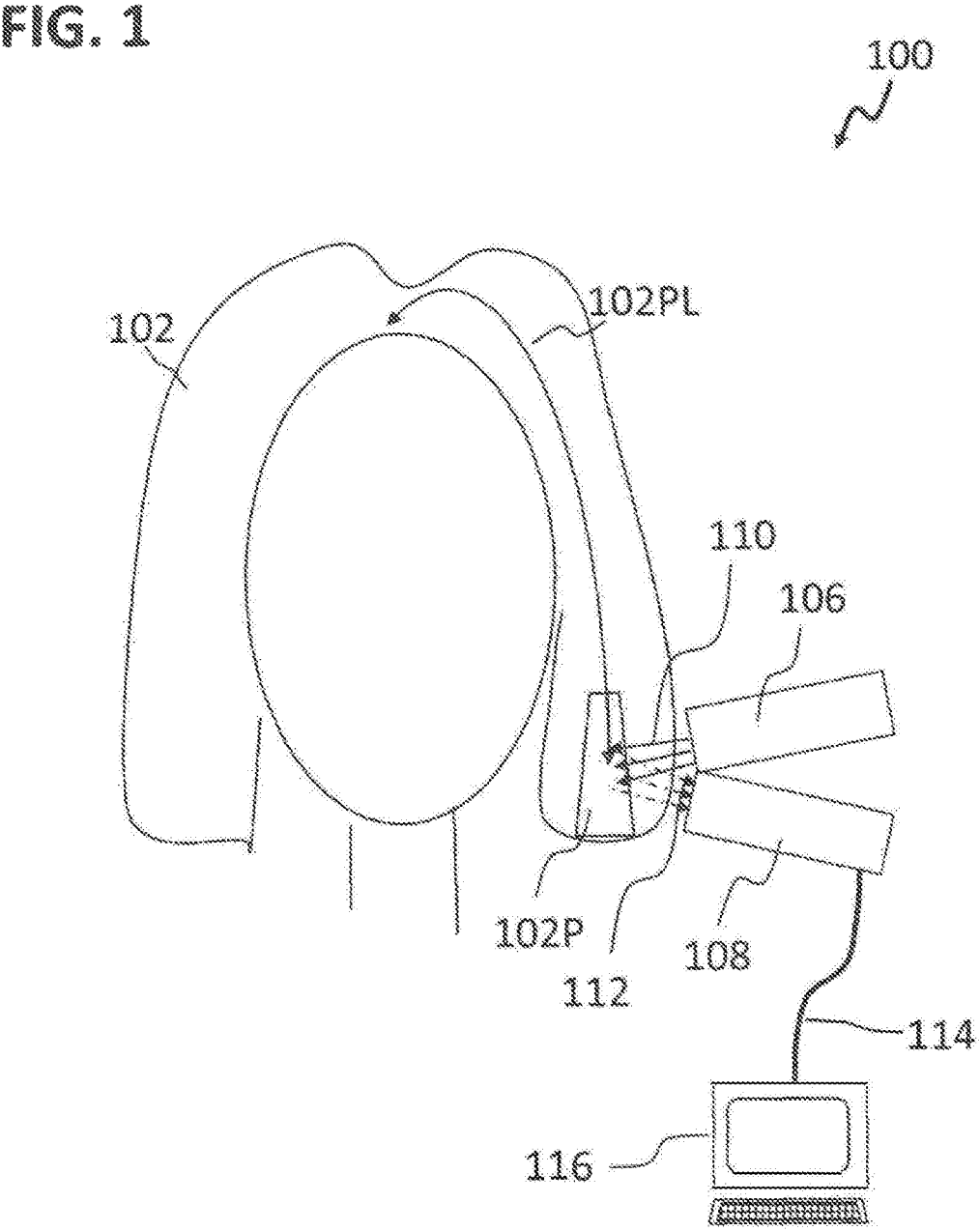
FIG. 1 shows a schematic depiction of a method and a device for determining a degree of damage of hair in accordance with various exemplary embodiments.

The following detailed description is merely exemplary in nature and is not intended to limit the disclosure or the application and uses of the subject matter as described herein.

Furthermore, there is no intention to be bound by any theory presented in the preceding background or the following detailed description.

In various exemplary embodiments an easy-to-use method and a corresponding device are provided which enable a precise determination of a degree of oxidative damage of hair with the aid of NIR spectroscopy and/or IR spectroscopy and multivariate calibration methods.

In various exemplary embodiments a mobile data processing device, for example a smart phone, a tablet or a laptop, can be used for the device and the method on the basis of a simple experimental procedure by use of novel miniaturised NIR sensors.

In various exemplary embodiments a method is also provided in order to provide suitable, possibly even personalised cosmetic products based on results of the method for determining a degree of damage. Here, in the case of personalisation, the method may also be suitable for execution in high numbers (what is known as "mass customisation" or "mass customised").

In various exemplary embodiments a near-infrared (NIR) and/or an infrared (IR) spectrum can be obtained, for example by employing ATR (attenuated total reflection) (near-) infrared spectroscopy. By use of mathematical models, a mathematical model can be created by measurement of calibration hair samples which have a cysteic acid content determined on the basis of a known analytical method which then allows a calculation of a content of cysteic acid and thus of hair damage in a hair sample, also referred to as a braid, from the consumer on the basis of the recorded NIR or IR spectrum. An analysis of the spectrum and use of the model can be performed here for example by employing known smart phones, tablets, or the like (with suitable apps).

A method for determining a degree of damage to hair is provided in different exemplary embodiments. Said method can comprise the following steps: during the exposure of a hair sample to near-infrared and/or infrared light, recording a spectrum of at least part of the near-infrared and/or infrared light that is reflected and/or scattered by the hair sample, comparing at least part of the spectrum with a spectroscopic calibration model obtained by employing near-infrared and/or infrared spectra and degrees of damage of a plurality of calibration hair samples, and determining the degree of damage to the hair using said comparison.

In various exemplary embodiments the method may also comprise the creation of the calibration model, wherein the creation of the calibration model may comprise the following steps: for the plurality of calibration hair samples, recording a calibration spectrum of at least part of the near-infrared and/or infrared light reflected and/or scattered by the calibration hair sample during exposure of the calibration hair sample to near-infrared and/or infrared light; determining a degree of damage of the calibration hair sample by employing an independent analytical method and allocating the degree of damage to the calibration spectrum; and determining a correlation between the plurality of calibration spectra and the plurality of degrees of damage.

In various exemplary embodiments the analytical method may include a determination of a cysteic acid content.

In various exemplary embodiments the determination of the cysteic acid content may include a chromatographic process.

In various exemplary embodiments the determination of a correlation between the plurality of calibration spectra and the plurality of degrees of damage may comprise the use of a partial least squares algorithm.

In various exemplary embodiments the at least part of the near-infrared and/or infrared light may comprise a (near-infrared) wave number range of from about 5,022 $cm^{-1}$ to about 4,020 $cm^{-1}$.

In various exemplary embodiments the at least part of the near-infrared and/or infrared light may comprise a (infrared) wave number range of around 1,040 $cm^{-1}$.

In various exemplary embodiments the at least part of the near-infrared and/or infrared light may comprise a (infrared) wave number range of from about 12,820 to about 7,692 $cm^{-1}$.

A device for determining a degree of damage to hair is provided in different exemplary embodiments. The device may comprise an NIR light source and/or an IR light source for exposing a hair sample to NIR and/or IR light, a spectrometer for recording at least part of a spectrum of NIR and/or IR light which has reacted with the hair sample, and a data processing device with a data memory, in which a spectroscopic calibration model obtained by employing a plurality of calibration hair samples is stored, and with a processor for comparing at least part of the spectrum with the spectroscopic calibration model and for determining the degree of damage of the hair on consideration of the comparison.

In various exemplary embodiments the NIR and/or IR light source and the spectrometer may form an integrated unit.

In various exemplary embodiments the at least part of the near-infrared and/or infrared light may comprise a (near-infrared) wave number range of from about 5,022 $cm^{-1}$ to about 4,020 $cm^{-1}$.

In various exemplary embodiments the at least part of the near-infrared and/or infrared light may comprise a (infrared) wave number range of around 1,040 $cm^{-1}$.

In various exemplary embodiments the integrated unit and/or the data processing device may be mobile devices.

A method for determining a user-specific hair treatment agent is provided in different exemplary embodiments. The method may comprise the steps of: determining a degree of damage of hair of a user in accordance with various exemplary embodiments; determining, in a computer-assisted manner, treatment results attainable by employing a plurality of hair treatment agents by employing predictive analytics on consideration of the determined degree of damage; and selecting the user-specific agent on the basis of the determined treatment results.

In accordance with various embodiments the user-specific hair treatment agent may include a haircare product, a hair colorant product, a bleaching product, or a styling product (for example for hair smoothing or permanent waving).

Exemplary embodiments as contemplated herein are shown in the drawings and will be explained in greater detail hereinafter.

Reference is made in the following detailed description to the accompanying drawings which form part of the present application and in which specific embodiments in which the present disclosure can be implemented are shown by way of illustration. It goes without saying that other embodiments can be used and structural or logical modifications can be made without departing from the scope of protection of the present disclosure. It goes without saying that the features of the various exemplary embodiments described herein can be combined with one another unless explicitly stated otherwise. The following detailed description therefore should not be interpreted in the limiting sense, and the scope of protection of the present disclosure is defined by the accompanying claims.

In the present description, the terms predictive analytics, big data and data mining are used synonymously.

In the present description, the term near-infrared (NIR) shall be used for light with a wave number in a range of from about 12,820 to about 4,000 cm$^{-1}$ and the term infrared (IR) shall be used for light with a wave number in a range of from about 3,999 to about 400 cm$^{-1}$.

A method described herein for determining a degree of damage of hair can be performed in accordance with various exemplary embodiments either with use of a near-infrared range, i.e. by employing irradiation of the hair with near-infrared light and spectral analysis of at least part of the NIR light after this has interacted with the hair, or with use of an infrared range, i.e. by employing exposure of the hair to infrared light and spectral analysis of at least part of the IR light once this has interacted with the hair, or with use of both the near-infrared and infrared range, i.e. by employing exposure of the hair to near-infrared and infrared light and spectral analysis of at least part of the NIR and at least part of the IR light once this has interacted with the hair.

A traditional method for determining a cysteic acid content of hair based on a chemical decomposition of the hair and subsequent chromatography of the released amino acids by employing high-pressure liquid chromatography (HPLC or high-pressure liquid chromatography).

Methods in the field of near-infrared spectroscopy have become established in recent years as alternatives. These methods allow a direct, destruction-free examination of the cysteic acid content and other constituents without complex sample preparation and without modifying the stricture of the hair or destroying the hair as a result of the analysis.

This can make it possible to attain results more quickly. In addition, it may be possible to subject the hair after the measurement to further treatments, such that repeated applications to a single hair strand can be performed.

It can be possible in addition to perform relatively simple measurements in various hair positions (for example hair near the scalp and hair distant from the scalp), for example also directly at the head without having to remove the hair sample.

Near-infrared spectroscopy can be used for example when sample preparation is difficult or impossible and multiple samples are to be analysed within a short space of time, for example in a pharmaceutical production for batch release or for measurements on skin or on other biological objects.

The near-infrared spectroscopy is based on a measurement of spectral absorption by vibration excitations of chemical bonds. Depending on what type of bond is involved, an absorption can take place at different wavelengths. Generally, the absorption can follow the Beer-Lambert law and can thus be proportional to the concentration of a constituent responsible for the absorption. Superimposing absorptions are additive, and therefore a quantification based on spectra is possible.

However, these absorptions can be harmonic (for example in the NIR range) or combination vibrations. An allocation of individual absorption wavelengths can thus be hindered.

For this reason, chemometric methods can be used for evaluation of the spectra and in particular for quantitative evaluation.

NIR spectroscopy can also therefore be suitable for taking a measurement on hair because in the case of near-infrared radiation not only is the surface of the hair analysed, but the hair can also be at least partially penetrated due to the small absorption cross-sections for the near-infrared radiation (for example compared to light in the visible wavelength range).

An evaluation of the spectra can be performed by employing a computing model which can be developed in a calibration phase and validation phase on the basis of a sufficiently large collective of comparison spectra. To this end it may be necessary that reference values of the characteristic variables to be calibrated are provided for all spectra. In the case of cysteic acid analytics performed on hair, these values can be obtained by employing the traditional HPLC method.

The computing model may be an artificial system that for example learns from the calibration hair samples and can generalise these once the learning phase is complete. This means that the examples are not simply memorised, but patterns and laws are identified in the learning data. Different approaches can be followed to this end. For example, a monitored learning, a partially monitored learning, an unmonitored learning, a corroborated learning and/or active learning can be used, in particular in conjunction with deep learning methods. Monitored learning can be implemented for example by employing an artificial neuronal network (for example a recurrent neuronal network) or by employing a support vector machine. Unmonitored learning can also be implemented for example by employing an artificial neuronal network (for example an autoencoder).

In various exemplary embodiments a measured near-infrared (NIR) range can have wave numbers of from approximately 12,820 cm$^{-1}$ to approximately 4,000 cm$^{-1}$. This wavelength range can include, inter alia, harmonic and combination vibrations for example of CH, OH and NH groups.

In various exemplary embodiments, NIR spectra of cystine in the wave number range of from approximately 6,200 cm$^{-1}$ to approximately 5,500 cm$^{-1}$ can represent characteristic absorption bands. If the hair changes, for example due to increasing damage (increase of the cysteic acid content), this can have an effect in the NIR spectrum on the bands at about 5,022 cm$^{-1}$ to about 4,020 cm$^{-1}$ characteristic for cysteic acid.

A chemometric analysis of the measured (N)IR spectra can be performed in various exemplary embodiments in an NIR wave number range of from approximately 8,000 cm$^{-1}$ to approximately 4,020 cm$^{-1}$ (at a resolution of for example 1 cm$^{-1}$) and/or in an IR wave number range of from about 1,100 cm$^{-1}$ to approximately 1,000 cm$^{-1}$ (at a resolution of for example 1 cm$^{-1}$). The relevant absorption bands of the component cysteic acid to be analysed can be found here, inter alia.

Besides the direct determination of the cysteic acid content via the characteristic absorption bands of cysteic acid, in particular in the range of from about 5,022 cm$^{-1}$ to about 4,020 cm$^{-1}$, an indirect determination of the cysteic acid content can also be performed. The indirect determination of the cysteic acid content is performed in a wave number range in which cysteic acid does not have any characteristic or relevant absorption bands.

There is an inverse correlation between the content of cysteic acid and the content of melanin in the hair, which makes it possible to determine the content of cysteic acid indirectly—via the determination of the melanin content. It has been found in particular that the process of oxidative damage (formation of cysteic acid) in the case of bleaching or dyeing of hair is linked to the breakdown of melanin.

The melanin occurring in the hair not only absorbs in the visible spectrum (VIS), but also in the short-wave near-infrared spectrum, i.e. up to approximately 1,300 nm. Without wishing to be linked to this theory, it is supposed that there is additionally a formation of specific oxidation products of melanin, which also have absorptions in the short-wave NIR range.

It has been found that reliable calibration models that produce a correlation between the short-wave near-infrared spectrum and the cysteic acid content of hair samples and which have substantially the same quality, and also evaluations over the entire or over longer-wave parts of the near-infrared and/or infrared spectral range, in particular longer-wave ranges with characteristic absorptions of the cysteic acid can be created also with the aid of short-wave near-infrared spectra with a wave number range of from about 12,820 to about 7,692 cm$^{-1}$, i.e. in a wave number range in which cysteic acid demonstrates no characteristic absorption.

To summarise, this means that the content of cysteic acid and therefore the determination of a degree of damage of keratin fibres can be determined indirectly via the content of melanin and optionally the oxidation products of melanin in the keratin fibres.

In various exemplary embodiments a measured near-infrared (NIR) range can have wave numbers of from approximately 12,820 cm$^{-1}$ to about 7,692 cm$^{-1}$.

In various exemplary embodiments a calibration model can be created on the basis of results of a quantitative computer-assisted evaluation (also referred to as chemometric analysis) for a plurality of calibration hair samples in combination with values for a cysteic acid content of the respective calibration hair sample obtained by employing an independent method, for example by employing HPLC, for said calibration hair samples. This can also be referred to as a calibration phase of the method for determining a degree of damage of hair.

If the calibration model is present, in various exemplary embodiments the concentration of cysteic acid (as measure for hair damage) can be very easily calculated from the spectra in comparison to the calibration spectra on the basis of a (N)IR spectrum obtained for a hair sample to be measured (also referred to as a measurement hair sample for distinction from the calibration hair samples, with the associated spectrum being referred to as the measurement spectrum). Here, the calibration model can allow both the calculation of the cysteic acid concentration if the measurement spectrum corresponds substantially to one of the calibration spectra (or variables determined from the spectra, for example a value for the absorption in the wavelength range characteristic for the cysteic acid, for example an equivalent breadth or the like, are substantially identical), and if the measurement spectrum or the variable determined therefrom were to be classified between two calibration spectra or beyond a calibration spectrum. In other words, on the basis of the discrete calibration spectra and the associated analytically determined cysteic acid concentration values, the calibration model can be formed as a continuous model which enables an inter- and extrapolation of the discrete data points.

In various exemplary embodiments the model formation, i.e. a quantitative evaluation of the calibration spectra and of the associated cysteic acid concentration values, can be performed on the basis of what is known as the partial least square method (PLS). For example, when creating the calibration model with the aid of a partial least squares (PLS) algorithm, a correlation between the spectroscopic data and the corresponding concentration values of the individual components (here, for example, of cysteic acid; if further hair constituents alternatively or additionally allow a conclusion of the degree of damage of the hair and demonstrate characteristic absorption features in the NIR or IR spectrum, these can be used alternatively or additionally to cysteic acid) can be calculated.

The more comprehensive is a database (i.e. the more spectra and associated reference values are provided), the better can be the prediction accuracy of the calibration model. Here, the values that were able to be quantified for the calibration hair samples in a laboratory via another independent analytical method (here for example HPLC after decomposition in order to determine the cysteic acid concentration) are referred to as reference values.

Within the scope of the model formation, virtual spectra—what are known as factors—can be determined from the correlation of spectra and reference values in accordance with various exemplary embodiments and can reflect the essential, component-related spectral components.

The spectra to be predicted can then be optimally assembled (fitted) with these factors in various exemplary embodiments. The weighting factors of the individual factors leading here to an optimal result can form the basis of the quantitative result calculation.

The following parameters can be used in accordance with various exemplary embodiments to optimise the PLS model: a frequency range used for the evaluation, a mathematical data pre-processing, a selection of the optimal factor number, and/or an elimination of outliers (spectral and/or concentration outliers).

In various exemplary embodiments a quality of the developed calibration model can be assessed on the basis of at least one static performance parameter. The at least one static performance parameter can be, for example, a correlation coefficient $R^2$ (also referred to as a coefficient of determination) and/or an analysis error of a RMSEP (root mean square error of prediction) cross validation.

In various exemplary embodiments a plurality of models can be created for the development of the calibration model and can each be validated within the scope of an optimisation, such that the model that enables the best prediction results can be determined as the calibration model. To this end, two different methods can be used: a computer-assisted cross validation and/or a validation with external reference samples.

In the case of a cross validation, test calibrations can be calculated from a sample set, with one of the samples being removed in each case. Each removed sample can then be calculated with this sub-calibration. If this procedure is now performed for all samples one after the other, a valid result set can thus be obtained from the individual samples thereof, the results of which are considered and are not included in the fundamental calibration set. The parameters of the particular optimisation step can be assessed on the basis of the results of this cross validation.

Alternatively or additionally, the validation can be performed on an independent validation data set. To this end, a plurality of independent validation samples with known analyte concentration (i.e. for example with known cysteic acid content) can be predicted with the aid of the chemometric calibration model. Here, "independent" means that the validation samples are not contained in the calibration data set. One disadvantage of this method can be considered to be the fact that the valuable validation samples cannot be used to improve the calibration.

Figure 3:
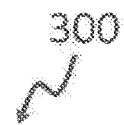
FIG. 3 shows a table with prediction results for a degree of damage of a plurality of hair samples which were obtained by employing a method in accordance with one exemplary embodiment.

For exemplary results of the determination of a degree of damage of hair in accordance with an exemplary embodiment and an associated validation, see the table in FIG. 3 and the associated description.

FIG. 1, in a view 100, shows a schematic depiction of a method for determining a degree of damage of hair in accordance with various exemplary embodiments.

In accordance with various exemplary embodiments, a hair sample 102P can be examined in order to determine a degree of damage of hair 102 of a user. The hair sample 102P can be left on the head or removed. The hair sample 102P can be at a distance 102PL from the head of the user or can be removed therefrom. The hair sample 102P can comprise a minimum amount of hair, which for example can be expressed as a minimum area which can be covered comprehensively by the (for example spread flat) hair sample 102P, for example at least about 1 cm$^2$, or for example as a minimum weight, for example at least about 0.5 g.

In various exemplary embodiments a device can be used to determine the degree of damage of hair 102, as shown schematically in FIG. 1 by way of example in a view 100.

In various exemplary embodiments the hair sample 102Pb can be spread such that it covers at least one region of interaction which is illuminated by a light source 106 with NIR and/or IR light 110 and from which the light 110, after interaction with the hair sample 102 and then referred to as light 112 to be analysed, enters a spectrometer 108.

In various exemplary embodiments the hair sample 102P can be illuminated with NIR light 110 and/or with IR light 110. The NIR light 110 can cover a wave number range of from approximately 1,280 cm$^{-1}$ to approximately 4,000 cm$^{-1}$, or at least a suitable partial range therefrom, for example from approximately 8,000 cm$^{-1}$ to approximately 4,020 cm$^{-1}$, for example from approximately 5,022 cm$^{-1}$ to approximately 4,020 cm$^{-1}$. A further preferred partial range covers wave numbers of from approximately 12,820 cm$^{-1}$ to 9,090 cm$^{-1}$ and particularly preferably from approximately 12,500 cm$^{-1}$ to 9,524 cm$^{-1}$. The IR light 110 can cover a wave number range of from approximately 3,999 cm$^{-1}$ to approximately 400 cm$^{-1}$, or at least a suitable partial range therefrom, for example from approximately 3,000 cm$^{-1}$ to approximately 500 cm$^{-1}$, for example from approximately 1,100 cm$^{-1}$ to approximately 1,000 cm$^{-1}$.

In various exemplary embodiments, a light source 106 of the NIR and/or the IR light 110 can be for example an NIR lamp and/or an IR lamp, or any other conventional light source that provides a suitable light spectrum.

In various exemplary embodiments, for example if an ATR spectroscopy is used, the light 110 emitted from the light source 106 can be guided in a medium in which it is reflected totally (for example a number of times). The hair sample 102P can be brought so close to the medium, for example into physical contact with the medium, that it can interact with evanescent light of the light 110, for example can absorb spectrally characteristic components of the light 110.

In various exemplary embodiments, other NIR and/or IR spectroscopy methods can be used, for example diffuse reflection spectroscopy (DRS).

In various exemplary embodiments, in the method for determining a degree of damage of hair that can be applied without destroying the hair sample (and for example can be performed even on hair left on the head of the user), the (N)IR radiation will reach only a surface region of the hair. A penetration depth of (N)IR radiation in hair can be typically approximately up to 10 µm, whereas a typical hair diameter can be approximately 60 to 70 µm. However, by employing the independent analysis of the cysteic acid content of the hair samples which is used for the formation of the calibration model, the surface properties of the calibration hair samples are correlated with the measure for the degree of damage of the hair (here for example the cysteic acid content), and therefore a prediction of the degree of damage of the hair overall is made possible for the measurement hair samples on the basis of the (N)IR spectrum, even if the (N)IR spectrum reflects just one property of the hair surface.

Thanks to a continued improvement of (N)IR spectroscopy devices, these can be provided in miniaturised, for example mobile form, for example as a unit which can comprise the light source 106 and the spectrometer 108 as integrated constituents.

The (N)IR spectroscopy devices can be provided for example in the form of hand-held spectroscopy devices or add-on spectroscopy devices.

An example of a suitable hand-held spectroscopy device is the "MicroNIR OnSite" from the company Viavi Solutions Inc. This spectroscopy device is supplied with power and controlled by a tablet or a laptop via a USB connection and enables a recording of the near-infrared and/or infrared spectra of the keratin fibres of an individual in real time with a measurement time of between about 0.25 and about 0.5 seconds. The spectroscopy device has two integrated vacuum tungsten lamps as light source and an InGaAs photodiode array with 128 pixels. The "MicroNIR OnSite" operates in a wave number range of from about 6,060 to about 10,526 cm$^{-1}$. The distance between the keratin fibres and the glass of the hand-held spectroscopy device can be between 0 and about 15 mm, wherein a distance of 3 mm is preferred.

In one embodiment as contemplated herein the entire method for determining an individualised hair treatment is performed by the tablet or the laptop which supplies power to and controls the "MicroNIR OnSite" spectroscopy device. Alternatively, the obtained spectroscopic data can be sent to a further (mobile) data processing device, in particular a further smart terminal, which them performs the method for determining an individualised hair treatment. The spectroscopic data can be transmitted for example wirelessly by employing WLAN (WiFi) or Bluetooth.

A further suitable hand-held spectroscopy device is the "i-Spec Nano" by the company B&W Tek. The spectroscopy device is supplied with power via a USB connection and a (mobile) data processing device connected thereto or via a battery. The spectroscopy device comprises a light source and operates in a wave number range of from about 4,545 to about 7,692 cm$^{-1}$. The spectroscopic data is transmitted to a (mobile) data processing device, which then performs the method for determining an individualised hair treatment, wirelessly by employing WLAN (WiFi) or Bluetooth.

The "Quality Spec Trek" hand-held spectroscopy device from the company ASD Inc. is also suitable. It operates in a wave number range of from about 28,571 to about 400 cm$^{-1}$.

A further suitable hand-held spectroscopy device is the "SCiO by Consumer Physics", which displays the spectroscopic data on a smart terminal with the aid of the integrated app "SpectroScan". The hand-held spectroscopy device operates in the short-wave range of NIR, more specifically at wave numbers from about 9,090 to about 14,285 cm$^{-1}$ (corresponds to about 700 to about 1100 nm). The measured data is evaluated with the aid of a cloud, in which a material database, chemometric models and algorithms are stored, for example.

Further hand-held spectroscopy devices are also obtainable from the company Attonics Systems which operate either in the wave number range from about 9,090 to about 26,315 cm$^{-1}$ (VIS-NIR) or from about 3,333 to about 10,000 cm$^{-1}$ (NIR). These spectroscopy devices are based on interferometers and have a high light throughput and a high spectral resolution (<5 nm for VIS-NIR spectroscopy device and <20 nm for the NIR spectroscopy device). The spectroscopy devices have a multi-phase shift array (MPA) chip and an optical arrangement in a circular tube. The spectroscopy devices are also compatible with mobile data processing devices.

Further examples of VIS-NIR spectroscopy devices are the miniature spectroscopy devices "USB2000-VIS-NIR" and "USB4000-VIS-NIR" from the company Ocean Optics. These spectroscopy devices operate with a wavelength range of from about 350 to about 1,000 nm. The spectrometers are connected via a USB connection to a data processing device.

A further suitable, miniaturised NIR spectroscopy device can be found integrated in the smart phone H2 from the company Changhong.

In addition, there are a series of NIR sensors or NIR evaluation modules that can be used in hand-held spectroscopy devices. Suitable NIR evaluation modules are the "DLP® NIRscan" and "DLP® NIRscan Nano" modules from the company Texas Instruments. These have two tungsten lamps and InGaAs photodiodes as detectors. The module "DLP® NIRscan" operates in a wave number range of from about 4,016 to about 7,407 cm$^{-1}$ and the module "DLP® NIRscan Nano" in the range of from 5,882 to 11,111 cm$^{-1}$. The spectroscopic data is communicated wirelessly via Bluetooth Low Energy. With the aid of "Software Developer Kits" (SDK), for example the Open Source SDK from KST Technologies, apps can be developed which evaluate or further process the spectroscopic data.

Further suitable NIR sensors are obtainable under the name "NeoSpectra" from Si-Ware Systems. Specific sensors include: NeoSpectra SW62221-1.7, NeoSpectra SW62221-2.1 and NeoSpectra SW62221-2.5, which operate in different wave number ranges.

In various exemplary embodiments, the spectrum can transmit to a data processing device 116. This is denoted by reference sign 114. The transmission can take place over a known path, for example by employing a data cable, wireless data transmission (for example Bluetooth, WLAN, Thread, ZigBee or Near Field Communication (NFC)), or transmission can occur within a device if the spectrometer (and optionally the light source) is part of a data processing device (for example mobile telephone, tablet, laptop), or conversely the spectrometer 108 is formed with an integrated data processing device 116.

To receive and further process the data and for the model formation, the data processing device can be equipped in various exemplary embodiments with an appropriate software, for example an app.

In various exemplary embodiments a cysteic acid content of the hair sample can be determined as described above on the basis of the recorded (N)IR spectrum in conjunction with the calibration model.

In various exemplary embodiments the degree of damage can be determined within a categorical scale (for example light, medium, heavy).

In various exemplary embodiments the degree of damage can be determined within a metric scale (for example percentage of the content of cysteic acid).

In various exemplary embodiments the described method for determining a degree of damage of hair can be performed by employing a data processing device 116.

The data processing device, as described above in conjunction with FIG. 1, can comprise for example a mobile data processing device, for example a smart phone, a tablet or a laptop, but also another computer, such as a smart mirror, or any other data processing device that is suitable for storing and providing data, performing the comparison, and applying the model, possibly also creating the model, i.e. for example any data processing device with a sufficiently large data memory and sufficiently powerful processor.

In various exemplary embodiments the data processing device can also be designed to determine an individual hair treatment instruction depending on the determined degree of damage. The individual hair treatment instruction can comprise the recommendation of commercially obtainable bleaching agents and/or hair dyes and/or haircare products and/or hair styling products. Alternatively, the individual hair treatment instruction can consist for example in determining the chemical composition of a hair treatment agent, in particular a bleaching agent, a hair dye, a haircare product and/or hair styling product.

In various exemplary embodiments the data processing device may comprise an input device for inputting information into the data processing device, for example for inputting cysteic acid content measurement values for the calibration and optionally for inputting instructions, parameters, etc. for carrying out the method.

In various exemplary embodiments the data processing device may comprise at least one output device for outputting information, for example for outputting results of the method. The results can be output graphically and/or acoustically.

In various exemplary embodiments the at least one output device may comprise a screen and/or a printer and/or a loudspeaker.

In various exemplary embodiments any program (for example an app) that provides a modelling functionality can be used for a modelling.

FIG. 2A shows an NIR spectrum 200 of cysteic acid, FIG. 2B shows an IR spectrum 201 of cysteic acid, in each case as absorption units depending on the wave number.

By employing boxes 220, 222, in the NIR spectrum 200 in FIG. 2A (box 220) and in the IR spectrum 201 in FIG. 2B, spectral regions are highlighted which may have absorption features characteristic for cysteic acid. By way of example, in FIG. 2A the range of from approximately 5,022 cm$^{-1}$ to approximately 4,020 cm$^{-1}$ is highlighted, and in FIG. 2A the range of from approximately 1,100 cm$^{-1}$ to approximately 1,000 cm$^{-1}$.

These spectral ranges can be used in various exemplary embodiments for the method for determining a degree of damage of hair.

Alternatively or additionally, other or further NIR and/or IR spectral ranges can be used which have absorption features characteristic for cysteic acid.

FIG. 3 shows a table 300 with prediction results for a degree of damage of a plurality of hair samples (as cysteic acid content in % by weight) which were obtained by employing a method in accordance with one exemplary embodiment.

A cross validation and a validation were performed on an independent validation data set for an assessment of the quality of the calibration model used to determine the prediction results shown in table 300 in the third column.

The creation of calibrations for the quantification of cysteic acid was performed in this example substantially on the basis of Kerling hair patterns that were measured before and after various treatments.

In order to obtain a sufficiently large database, samples were collected over a longer period of time, the spectra were measured and then corresponding reference values were added. The quality of the developed model is described by the specification of a correlation coefficient $R^2$ and an analysis error of the RMSEP cross validation as statistical performance parameter.

For the creation of the calibration model in this example, the 1st Norris derivative and a reduced spectral range of from about 5,022 $cm^{-1}$ to about 4,020 $cm^{-1}$ was used as data pre-processing.

The PLS calibration achieves the following characteristic variables in the cross validation: a correlation coefficient of $R^2$=99.3% and a RMSEP value of on average 0.329 with 8 factors with Norris derivative as data pre-processing in the spectral range of from about 5,022 $cm^{-1}$ to about 4,020 $cm^{-1}$.

In order to test the quality of the method by external validation, "independent", non-calibrated spectra of test samples were predicted with the calibration models and compared with the corresponding reference values determined by employing an independent analytical method (HPLC).

The results are shown in Table 300.

A standard deviation (root mean square error of deviation, RMSED) is 0.34% by weight in this example.

As is shown in this example, cysteic acid contents of new hair patterns can thus be determined with the described accuracies after model creation by employing NIR measurements.

In various exemplary embodiments the described method could be performed alternatively or additionally to the NIR range by employing the IR range.

FIG. 4 shows a flow diagram 400 illustrating a method for determining a degree of damage of hair in accordance with various exemplary embodiments.

In various exemplary embodiments the method can comprise the following steps: during the exposure of a hair sample to near-infrared and/or infrared light, recording a spectrum of at least part of the near-infrared and/or infrared light with which the hair sample has interacted (at 410); comparing at least part of the spectrum with a spectroscopic calibration model obtained by employing near-infrared and/or infrared spectra and degrees of damage of a plurality of calibration hair samples (at 420); and determining the degree of damage to the hair using said comparison (at 430).

FIG. 5 shows a flow diagram 500 illustrating a method for determining a user-specific hair treatment agent in accordance with various exemplary embodiments.

In various exemplary embodiments the above-described method for determining a degree of damage of hair or the above-described device for determining a degree of damage of hair can be used for a method for determining a user-specific hair treatment agent.

In various exemplary embodiments the method for determining a user-specific hair treatment agent may comprise the steps of: determining a degree of damage of hair of a user in accordance with one of the above-described exemplary embodiments (at 510); determining, in a computer-assisted manner, treatment results attainable by employing a plurality of hair treatment agents by employing predictive analytics on consideration of the determined degree of damage (at 520); and selecting the user-specific agent on the basis of the determined treatment results (at 530).

Predictive analytics can be described generally as a method for extracting information from large data volumes and generating a model on the basis of this data, which model makes it possible to make predictions also for values which are not part of the dataset. When applying a method based on predictive analytics, some of the dataset can typically be used as a training dataset (also referred to as a training set or training data). This training dataset can then be used to generate one or more models which can then be tested on the basis of the data not part of the training dataset, on the basis of the data as a whole, or on the basis of a specially selected part of the data.

For an assessment of the model, i.e. a determination of the goodness of fit, a coefficient of determination $R^2$, a mean absolute error, a mean squared error, a standard deviation and/or a mean deviation can be used, for example.

The coefficient of determination $R^2$ can correspond to a squared correlation coefficient for a linear regression model. For another model (another relationship), it can be defined differently.

In accordance with various exemplary embodiments, various functions or methods can be used for the modelling by employing predictive analytics. In a simple case, a multiple linear regression can be used for example. Improved results can be attained typically with use of polynomial regressions, neuronal networks, support vector machines, decision trees (for example tree ensembles), or the like.

In various exemplary embodiments the method for determining a user-specific hair treatment agent can use, as independent parameter for the modelling by employing predictive analytics, a degree of damage of the hair of the user determined in accordance with a method for determining a degree of damage of hair as described in various exemplary embodiments. In addition, further independent parameters, for example a base hair color of the user, a degree of greying, etc., and as dependent parameter for example a desired treatment result, for example a desired hair color and/or desired hair structure, etc., can be used.

On the basis of these parameters, a user-specific hair treatment agent can be determined by employing predictive analytics, which agent attains or at least comes as close as possible to attaining the dependent parameter, for example the desired treatment result, under consideration of the independent parameters In various exemplary embodiments the user-specific hair treatment agent may include a haircare product, a hair colorant product, a bleaching product, or a styling product, for example a smoothing agent, such as a straightener or relaxer, or an agent for permanent waving.

Further advantageous embodiments of the method are clear from the description of the device, and vice versa.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. A method for determining a degree of damage of hair, comprising the following steps:
  during exposure of a hair sample to near-infrared or infrared light, recording a spectrum of at least part of the near-infrared or infrared light, respectively, that has interacted with the hair sample;

comparing at least part of the spectrum with a spectroscopic calibration model obtained by near-infrared (NIR) or infrared (IR) spectra and degrees of damage of a plurality of calibration hair samples; and determining the degree of damage of the hair on consideration of the comparison, wherein the spectroscopic calibration model is created by:
(i) for each of the plurality of calibration hair samples:
during the exposure of each calibration hair sample to NIR or IR light, recording a calibration spectrum of at least part of the NIR or IR light, respectively, that has interacted with the calibration hair sample,
determining the degree of damage of the calibration hair sample by a determination of a cysteic acid content, and
allocating the degree of damage to the calibration spectrum; and
(ii) determining a correlation between the plurality of calibration spectra and the plurality of degrees of damage,
wherein the determination of the cysteic acid content comprises a chromatographic process.

2. The method according to claim 1, wherein the determination of a correlation between the plurality of calibration spectra and the plurality of degrees of damage comprises the use of a partial least squares algorithm.

3. The method according to claim 1, wherein the at least part of the NIR or IR light comprises a wave number range of from 5,022 $cm^{-1}$ to 4,020 $cm^{-1}$.

4. The method according to claim 1, wherein the at least part of the NIR or IR light comprises a wave number range of from 12,820 $cm^{-1}$ to 7,692 $cm^{-1}$.

5. A method for determining a user-specific hair treatment agent, comprising the steps of:
determining a degree of damage of hair of a user according to claim 1;
determining, in a computer-assisted manner, treatment results attainable by employing a plurality of hair treatment agents by predictive analytics on consideration of the determined degree of damage; and
selecting the user-specific agent on the basis of the determined treatment results.

6. The method according to claim 5, wherein the user-specific hair treatment agent comprises a haircare product or a hair colorant product, a bleaching product, or a styling product.

7. The method according to claim 6, wherein the styling product comprises a smoothing agent, in particular a straightener or relaxer, or an agent for permanent waving.

8. A device for determining a degree of damage of hair, comprising:
an NIR light source or an IR light source for exposing a hair sample to NIR or IR light, respectively;
a spectrometer for recording a spectrum of at least part of the NIR or IR light that has interacted with the hair sample; and
a data processing device with a data memory, in which a spectroscopic calibration model obtained by NIR or IR spectra and degrees of damage of a plurality of calibration hair samples is stored, and with a processor for comparing at least part of the spectrum with the spectroscopic calibration model and for determining the degree of damage of the hair on consideration of the comparison,
wherein the spectroscopic calibration model is created by:
(i) for each of the plurality of calibration hair samples:
during the exposure of each calibration hair sample to NIR or IR light, recording a calibration spectrum of at least part of the NIR or IR light, respectively, that has interacted with the calibration hair sample,
determining the degree of damage of the calibration hair sample by a determination of a cysteic acid content, and
allocating the degree of damage to the calibration spectrum; and
(ii) determining a correlation between the plurality of calibration spectra and the plurality of degrees of damage,
wherein the determination of the cysteic acid content comprises a chromatographic process.

9. The device according to claim 8, wherein the NIR or IR light source and the spectrometer form an integrated unit.

10. The device according to claim 9, wherein the integrated unit or the data processing device are mobile devices.

11. The device according to claim 8, wherein the at least part of the NIR or IR light has a wave number range of from 5,022 $cm^{-1}$ to 4,020 $cm^{-1}$.

12. The device according to claim 8, wherein the at least part of the NIR or IR light has a wave number range of from 12,820 $cm^{-1}$ to 7,692 $cm^{-1}$.

13. The device according to claim 8, wherein the data processing device is also designed to determine an individual hair treatment instruction depending on the determined degree of damage.

* * * * *